United States Patent [19]

Eramo et al.

[11] Patent Number: 4,665,760

[45] Date of Patent: May 19, 1987

[54] MOUNTING AND TRAVERSING ASSEMBLY FOR IN SITU PARTICLE SIZE MEASURING DEVICE

[75] Inventors: Mark P. Eramo, Enfield, Conn.; John M. Holmes, Southwick, Mass.

[73] Assignee: Combustion Engineering, Inc., Windsor, Conn.

[21] Appl. No.: 828,479

[22] Filed: Feb. 12, 1986

[51] Int. Cl.⁴ ............................................. G01F 15/18
[52] U.S. Cl. ................................................. 73/866.5
[58] Field of Search ................ 73/431, 863.85, 866.5, 73/865.5; 248/657; 356/336, 338, 343, 340

[56] References Cited

U.S. PATENT DOCUMENTS

| | | | |
|---|---|---|---|
| 3,005,347 | 10/1961 | Smithson | 73/863.55 |
| 3,719,886 | 3/1973 | Vanderberg et al. | 324/175 |
| 3,831,618 | 8/1974 | Liston | 73/864.22 |
| 4,151,466 | 4/1979 | Boyer et al. | 324/175 |
| 4,152,070 | 5/1979 | Kushner et al. | 356/343 |
| 4,387,592 | 6/1983 | Welker | 73/432 B |
| 4,494,403 | 1/1985 | Bowers et al. | 73/863.58 |
| 4,538,472 | 9/1985 | Skarpness | 73/863.55 |
| 4,595,291 | 6/1986 | Tatsuno | 356/343 |

OTHER PUBLICATIONS

Particle and Droplet Sizer, Powder Metallurgy International, vol. 10, No. 2, May 1978, p. 99.

*Primary Examiner*—Stewart J. Levy
*Assistant Examiner*—Robert R. Raevis
*Attorney, Agent, or Firm*—Arthur E. Fournier, Jr.

[57] ABSTRACT

A mounting and traversing assembly (10) particularly suited for employment with an in situ particle size measuring device. The subject mounting and traversing assembly (10) includes an enclosure (12) operative as a housing and/or support surface for other components of the mounting and traversing assembly (10); support means (14) operative to support for movement within the enclosure (12) the probe portion (62) of the particle size measuring device with which the mounting and traversing assembly (10) is being utilized; guide means (16) operative to guide the support means (14) during the movement thereof within the enclosure (12); movement imparting means (18) operative for imparting motion to the support means (14); motor means (20) operative as the power source for the movement imparting means (18); position indicating means (22,24) operative to provide an indication of the position of the probe portion (62) of the particle size measuring device; and mounting means (26) operative for effecting the installation of the mounting and the traversing assembly (10).

6 Claims, 6 Drawing Figures

MOUNTING AND TRAVERSING ASSEMBLY FOR IN SITU PARTICLE SIZE MEASURING DEVICE

CROSS-REFERENCE TO RELATED APPLICATIONS

This application is hereby cross-referenced to the following two patent applications which were commonly filed herewith and which are commonly assigned: U.S. patent application Ser. No. 828,480 filed Feb. 12, 1986, entitled "An In Situ Particle Size Measuring Device", filed in the names of James M. Niziolek and James P. Sutton; and U.S. patent application Ser. No. 828,490 filed Feb. 12, 1986, entitled "Pulverized Solid Control System", filed in the names of George F. Shulof and Michael J. DiMonte.

BACKGROUND OF THE INVENTION

This invention relates to mounting and/or traversing devices, and more specifically to a mounting and traversing device which is particularly suited for employment with an in situ particle size measuring device.

One of the important parameters in many industrial processes is particle size. As such, it has long been known in the prior art to provide devices that are capable of being employed for purposes of effecting measurements of particles. To this end, the prior art is replete with examples of various types of devices that have been used to obtain measurements of particles. In this regard, in many instances discernible differences exist in the technique by which the measurement of the particles is accomplished. The existence of such differences is, in turn, attributable for the most part to the diverse functional requirements that are associated with the specific application in which such devices are designed to be employed. For instance, in the selection of the particular type of device that is to be utilized for a specific application one of the principal factors to which consideration must be given is that of the nature of the substance of which the particle that is to be measured is formed. Another factor to which consideration must be given is that of the nature of the substance in which the particles are present at the time they are being measured. Yet another factor to which consideration must be given is the relative size of the particles that are to be measured.

Some of the techniques that have been utilized heretodate by the prior art for purposes of accomplishing the measurement of particles include acoustical techniques, optical counting techniques, electrical counting techniques, sedimentation techniques, separation techniques and surface measurement techniques. Moreover, the kinds of particles with which such techniques have been sought to be applied for purposes of making measurements of the particles include such particles as blood particles, food particles, chemical particles, mineral particles as well as others. In addition, diverse ones of the techniques to which reference has been had hereinbefore have been sought to be employed for purposes of accomplishing the measurement of particles while the latter are present in a variety of different types of fluid substances such as various types of gases and various types of liquids.

Unfortunately, however, the devices that have been available in the prior art heretofore for purposes of enabling the techniques to be carried out which have been referred to above have been found to be disadvantageously characterized in one or more respects. To this end, where such devices have been sought to be employed in connection with applications involving industrial processes for purposes of generating information relating to particle size that could be utilized to accomplish, as needed, adjustments to the industrial process, it has not been possible through the use of prior art forms of devices to generate the information required in a sufficiently fashion and/or with the desired degree of accuracy. Namely, it has proven to take far too long and/or to require far too much effort to generate the desired information pertaining to particle size for this information to be of any significant value insofar as concerns the utilization thereof for purposes of making timely adjustments to the industrial process. In large measure this is based on the fact that with the prior art devices that have heretofore been available for use for purposes of effectuating particle size measurements it has not been possible to make measurements in situ therewith. As a result, in order to make use of the prior art devices that have been available heretofore there has most often existed a need to collect a sample from the medium in which are present the particles that it is desired to measure, a need to transport this sample to the device that is to be used to accomplish the particle size measurements, a need to actually perform the particle size measurements with the device, and then finally based on the results of the particle size measurements effectuate whatever adjustments must be made to the industrial process in order to ensure that the particles do in fact embody the size that they must have if the particular industrial process from which the particles that were measured were taken is to be successfully operated.

By way of exemplification and not limitation, one form of industrial process in which particle size is known to be an important consideration for the successful operation of the process is the combustion of pulverized coal. As regards the combustion of pulverized coal, it has long been known that an essential component of any steam generation system that utilizes pulverized coal as a fuel is the apparatus in which the coal is pulverized in order to render the coal suitable for such usage. One form of apparatus in particular that has frequently been used for purposes of accomplishing the pulverization of coal, although various types of apparatus have been known to have been employed for this purpose, is that which those in the industry commonly refer to as a bowl mill. The bowl mill obtains its name principally from the fact that the pulverization, i.e., grinding, of the coal that takes place therewithin occurs on a grinding surface which in configuration bears a resemblance somewhat to that of a bowl. By way of illustration, reference may be had to U.S. Pat. No. 3,456,971, which issued Sept. 9, 1969 to J. F. Dalenberg et al and which is assigned to the same assignee as the present invention, for a showing of a prior art form of bowl mill. This patent contains a teaching of both the nature of the construction and the mode of operation of a bowl mill that is suitable for use for purposes of effectuating the pulverization of the coal that is used to fuel a coal-fired steam generator.

The efficient combustion of pulverized coal, particularly as it relates to the use of pulverized coal as a fuel in a steam generation system, requires that the coal particle size be held close to a specified particle size distribution. Typically, for a medium reactivity coal this is 70% passing through 200 mesh, and 1% not passing through 50 mesh. Based on an economic evaluation for a typical 500 MW coal-fired steam generator power plant, it has been determined that through an increase in carbon conversion rate which in turn is achievable by maintaining a specified particle size distribution, it is possible to realize significant savings amounting to hundreds of thousands of dollars on an annualized basis in the cost of operating a power plant of the size to which reference has been made hereinbefore. Obviously, however, the savings that will be actually realized insofar as any specific power plant that is fueled with pulverized coal is concerned by virtue of maintaining the coal particle size close to a specified particle size distribution will be dependent on a number of factors including the reaction kinetics of the coal, i.e., how sensitive the combustion efficiency is to particle size for the specific coal being used, and how well and often control is exercised over the bowl mill to maintain the optimum size distribution of the coal particles. In every instance, however, maintaining the size distribution of the coal particles close to the optimum should result in some measure of fuel savings.

Other benefits should also flow from the fact that better control is being exercised over the size distribution of the coal particles. In this regard, reference is had to the fact that there should be reduced slagging in the steam generator due to better control over the size distribution of the coal particles. In addition, it may be possible in some instances to make use of the fact that deviations are occurring in the size distribution of the coal particles from that which should be present as a maintenance and diagnostic aid to detect problems associated with the operation of the bowl mill in which the pulverization of the particles of coal that have been measured was effected. Also, the possibility exists for exercising continuous control over the operation of the bowl mill through the use of the information garnered from having made coal particle size measurements. Yet another possibility is to utilize the information acquired from the performance of coal particle size distribution measurements for purposes of obtaining an indication of the fuel-to-air ratio in the coal feed pipe by means of which, as is well-known to all, the pulverized coal particles are conveyed from the bowl mill to the steam generator wherein the combustion of the pulverized coal particles takes place.

Thus, there has been evidenced in the prior art a need for a new and improved form of mounting device suitable for use for purposes of effecting the mounting of a particle size measuring device such that measurements relating to particle size can be made in situ therewith. Moreover, a need has thus been evidenced in the prior art for a new and improved form of traversing device which would be suitable for use for purposes of enabling a particle size measuring device to be traversed across a flow stream in which particles are present so that measurements can be obtained of these particles as the particle size measuring device is being traversed across the flow stream. Further, a need has been evidenced in the prior art for a new and improved form of mounting and traversing device which is capable of being subjected to rugged handling without being adversely affected thereby. In addition, a need has been evidenced for a new and improved form of mounting and traversing device which is characterized by the fact that when employed with a particle size measuring device the mounting and traversing device is operative to maintain the proper alignment of the particle size measuring device while the latter is being employed for purposes of making particle size measurements. Also a need has been evidenced for a new and improved form of mounting and traversing device which is characterized by the fact that the device is capable of being installed easily and rapidly.

It is, therefore, an object of the present invention to provide a new and improved mounting and traversing assembly suitable for use with devices wherein in connection with the operation thereof the devices are required to be mounted and traversed.

It is another object of the present invention to provide such a mounting and traversing assembly which is particularly suited for employment with particle size measuring devices wherein it is desired through the use of the particle size measuring devices to obtain therewith measurements in situ of particle size.

It is still another object of the present invention to provide such a mounting and traversing assembly which is suited for employment for purposes of effecting the mounting and traversing of a particle size measuring device particularly in applications in which concern over the wear occasioned by the positioning of the particle size measuring device in the flow stream of the fluid medium containing the particles to be measured, if the particle size measuring device were to be permanently positioned therein, is a consideration.

A further object of the present invention is to provide such a mounting and traversing assembly which is suited for employment for purposes of effecting the mounting and traversing of a particle size measuring device particularly in applications in which because the width of the flow stream of the fluid medium in which the particles are entrained is sufficiently large as to render it desirable to make measurements with the particle size measuring device of particles at various locations within the aforereferenced flow stream.

A still further object of the present invention is to provide such a mounting and traversing assembly which is particularly suited for employment with a particle size measuring device and which is characterized by the fact that the mounting and traversing assembly is capable of being subjected to rugged handling without being adversely affected thereby.

Yet another object of the present invention is to provide such a mounting and traversing assembly which is particularly suited to be employed with a particle size measuring device and which is characterized by the fact that when employed with a particle size measuring device such a mounting and traversing assembly is operative to maintain the proper alignment of the particle size measuring device while the latter is being employed for purposes of making particle size measurements.

Yet still another object of the present invention is to provide such a mounting and traversing assembly which is particularly suited to be employed with a particle size measuring device, and when being so employed is characterized by the fact that the mounting and traversing assembly is capable of being installed easily and rapidly, while yet being relatively inexpensive to provide.

SUMMARY OF THE INVENTION

In accordance with the present invention there is provided a mounting and traversing assembly which is particularly suited for employment with an in situ particle size measuring device. The subject mounting and traversing assembly includes an enclosure, a ball screw, a shaft, a drive arm, support means for the probe portion of the particle size measuring device, gear motor means, support means for the gear motor means, first position indicating means, second position indicating means, and mounting means for effecting the installation of the mounting and traversing assembly. The ball screw is suitably mounted within the enclosure so as to extend along a first side thereof for substantially the length thereof. The shaft is suitably mounted within the enclosure so as to extend in parallel relation to the ball screw along a second side of the enclosure for substantially the length of the enclosure. The support means for the probe portion of the particle size measuring device is interposed between the ball screw and the shaft, and is operative to support the probe portion of the particle size measuring device within the enclosure for movement relative thereto. The drive arm is suitably secured to the support means for the probe portion of the particle size measuring device. In addition, the drive arm is operatively connected to both the ball screw and the shaft whereby rotation imparted to the ball screw is transmitted in turn to the drive arm and therethrough to the probe portion of the particle size measuring device such that the rotational motion of the ball screw becomes transformed into linear motion of the probe portion of the particle size measuring device. The gear motor means is supported on the enclosure in juxtaposed relation to the ball screw by means of the support means for the gear motor means. The gear motor means is operatively connected to the ball screw so as to be operative to impart rotation thereto. A first position indicating means is supported within the enclosure so as to be cooperatively associated with the ball screw. The first position indicating means is operative to provide an indication of the position occupied at any given point in time by the probe portion of the particle size measuring device. A second position indicating device is supported within the enclosure so as to be cooperatively associated with the shaft. The second position indicating means is operative to provide an indication of when the probe portion of the particle size measuring device has reached the limit of its travel both in a first direction and in a second direction. The mounting means for effecting the installation of the mounting and traversing assembly is designed to be operative to enable the mounting and traversing assembly to be detachably installed whereby the probe portion of the particle size measuring device is capable of being suitably located for purposes of accomplishing therewith the particle size measurements desired.

DESCRIPTION OF A PREFERRED EMBODIMENT

Figure 1:
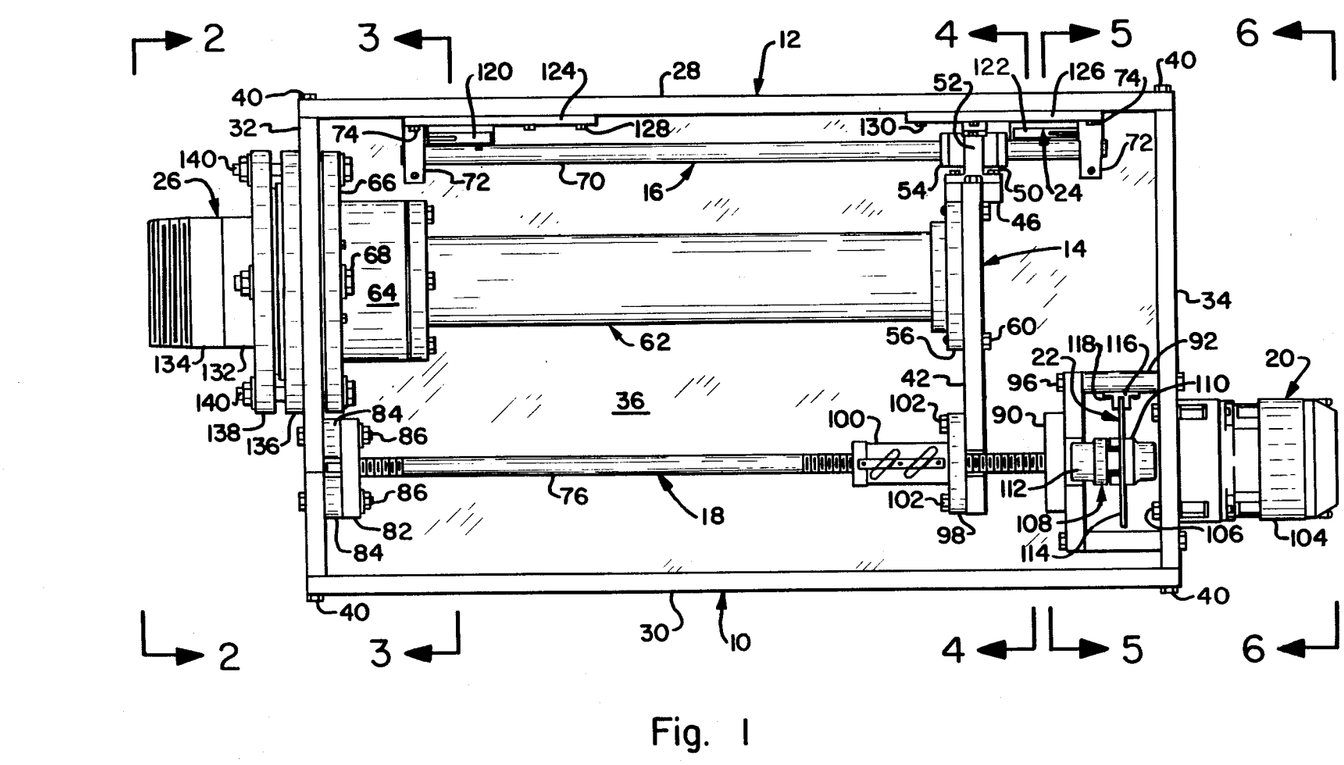
FIG. 1 is a top plan view with the cover removed of a mounting and traversing assembly constructed in accordance with the present invention.

Referring now to the drawing, and more particularly to FIG. 1 thereof, there is depicted therein a mounting and traversing assembly, generally designated by the reference numeral 10, constructed in accordance with the present invention. The mounting and traversing assembly 10 is particularly suited for employment with particle size measuring devices wherein it is desired through the use of the particle size measuring devices to obtain therewith measurements in situ of particle size. As best understood with reference to FIG. 1 of the drawing, the mounting and traversing assembly 10 embodies the following major components: an enclosure, generally designated by the reference numeral 12, operative as a housing and/or support surface for other components of the mounting and traversing assembly 10; support means, generally designated by the reference numeral 14, operative to support for movement within the enclosure 12 the probe portion of the particle size measuring device with which the mounting and traversing assembly 10 is being utilized; guide means, generally designated by the reference numeral 16, operative to guide the support means 14 during the movement thereof within the enclosure 12; movement imparting means, generally designated by the reference numeral 18, operative for imparting motion to the support means 14; motor means generally designated by the reference numeral 20, operative as the power source for the movement imparting means 18; first position indicating means, generally designated by the reference numeral 22, operative to provide an indication of the position occupied at any given point in time by the probe portion of the particle size measuring device; second position indicating means, generally designated by the reference numeral 24, operative to provide an indication of when the probe portion of the particle size measuring device has reached the limit of its travel in either of two directions; and mounting means generally designated by the reference numeral 26, operative to enable the mounting and traversing assembly 10 to be detachably installed whereby the probe portion of the particle size measuring device is capable of being suitably located for purposes of accomplishing therewith the particle size measurements that are desired.

In order to best understand the nature of the construction and the mode of operation of the mounting and traversing assembly 10, it is believed desirable to set forth herein a description of the mounting and traversing assembly 10 in the context of the latter being employed with a particular form of particle size measuring device. To this end, the particular particle size measuring device, which has been selected for use for this purpose, is that which forms the subject matter of U.S. patent application Ser. No. 828,480, which is assigned to the same assignee as the present application and which was filed concurrently herewith. For purposes of obtaining an understanding of the mounting and traversing assembly 10 of the present invention it is not deemed necessary that there be set forth herein a detailed description of the particle size measuring device which forms the subject matter of U.S. patent application Ser. No. 828,480. Rather, it is deemed sufficient for purposes of obtaining an understanding of the mounting and traversing assembly 10 of the present invention that there be presented herein merely a description of the nature of the construction and the mode of operation of the components of the particle size measuring device with which the mounting and traversing assembly 10 cooperates. For a more detailed description of the nature of the construction and the mode of operation of the components of the aforesaid particle size measuring device which are not described in detail herein, one may have reference to U.S. patent application Ser. No. 828, 840.

Proceeding now with the description of the nature of the construction of the mounting and traversing assembly 10, the enclosure 12 thereof will first be described. In this connection, reference will be had in particular to FIGS. 1, 2 and 3 of the drawing. Referring thus to FIG. 1, the enclosure 12 includes a pair of side plates denoted by the reference numerals 28 and 30 in FIG. 1, a pair of end plates denoted by the reference numerals 32 and 34 in FIG. 1, a bottom plate denoted by the reference numeral 36 in FIG. 1, and a cover seen at 38 in FIGS. 2 and 3 of the drawing. The side plates 28, 30 are suitably joined to the end plates 32, 34 as well as to the bottom plate 36 such as by being fastened thereto. For this purpose, any suitable conventional form of fastening means may be employed such as the threaded fasteners which for ease of reference are each identified by the same reference numeral, i.e., reference numeral 40, in the drawing. Similarly, the cover 38 is suitably joined to the side plates 28, 30 as well as to the end plates 32, 34 such as by being fastened thereto through the use of any conventional form of fastening means. The threaded fasteners 40 to which reference has previously been had hereinbefore may also be utilized for this purpose; namely, accomplishing the fastening of the cover 38 to the side plates 28, 30 as well as to the end plates 32, 34.

Figure 4:
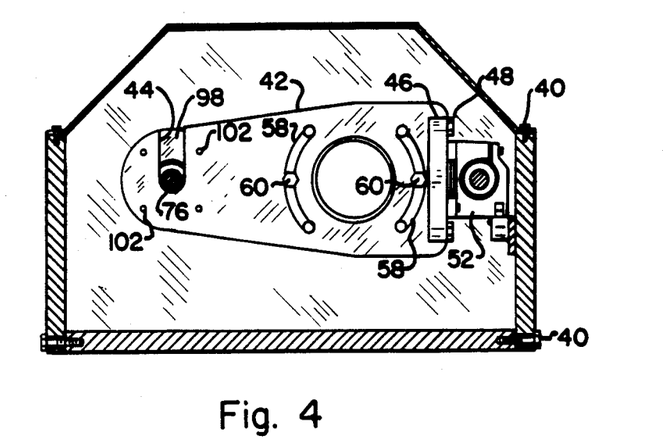
FIG. 4 is a cross-sectional view of the mounting and traversing assembly of FIG. 1 constructed in accordance with the present invention taken substantially along the line 4—4 in FIG. 1.

Considering next the support means 14, the latter is operative to support for movement within the enclosure the probe portion of the particular particle size measuring device with which the mounting and traversing assembly 10 is being utilized. A description will now be had of the nature of the construction of the support means 14. For this purpose, reference will be had in particular to FIGS. 1 and 4 of the drawing. As best understood with reference to FIGS. 1 and 4, the support means 14 includes a drive arm, the latter being denoted in FIGS. 1 and 4 by the reference numeral 42. The drive arm 42, in a manner yet to be described, is suitably supported intermediate the side plates 28 and 30 so as to extend substantially perpendicular thereto, and in substantially parallel relation to the end plates 32 and 34 such as to be located in closer proximity to the end plate 34 than to the end plate 32. With reference to FIG. 4, it can be seen therefrom that the drive arm 42 adjacent to one end thereof has formed therein a slot, identified by the reference numeral 44, which as will be described more fully hereinafter is suitably dimensioned so as to enable the movement imparting means 18 to be received therewithin for a purpose yet to be described. At the other end thereof, the drive arm 42 has a mounting bracket, identified by the reference numeral 46, secured thereto through the use of any conventional form of fastening means such as through the use of threaded fasteners, the latter being denoted by the reference numeral 48 in FIGS. 1 and 4. Secured in turn to the mounting bracket 46 by conventional threaded fasteners 50 is a pillow block, the latter being designated in FIGS. 1 and 4 by the reference numeral 52. In a manner well-known to those skilled in the art, the pillow block 52 has cooperatively associated therewith a ball bushing, denoted by the reference numeral 54 in FIGS. 1 and 4. For a purpose which will be described more fully hereinafter, the ball bushing 54 is suitably dimensioned so as to be capable of receiving therewithin for sliding movement relative thereto the guide means 16.

Continuing with the description of the nature of the construction of the support means 14, the drive arm 42, as can best be seen from FIG. 1 of the drawing, also has secured thereto a flange, the latter being denoted by the reference numeral 56 in FIG. 1. More specifically, the flange 56 is mounted to the drive arm 42 so as to be positioned intermediate the slot 44 to which reference has been had hereinbefore and the previously described ball bushing 54. In accord with the best mode embodiment of the invention, preferably the flange 56 is adjustably secured to the drive arm 42. To this end, as best understood with reference to FIG. 4 of the drawing, the drive arm 42 has a pair of arcuate slots, denoted by the reference numeral 58 in FIG. 4, formed therein. Positioned within each of the arcuate slots 58 is a threaded fastener seen at 60 in both FIGS. 1 and 4. Each of the threaded fasteners 60 is in turn threadedly engaged in threaded openings (not shown) with which the flange 56 is suitably provided such that by varying the positions of the threaded fasteners 60 in the arcuate slots 58 it is possible to adjust the positioning of the flange 56 relative to the drive arm 42. As will become more evident from the description that follows hereinafter the purpose in being able to adjust the positioning of the flange 56 relative to the drive arm 42 is to enable the probe portion, generally designated by the reference numeral 62 in FIG. 1 of the drawing, of the particle size measuring device with which the mounting and traversing assembly 10 of the present invention is being utilized to be properly aligned in order to accomplish the desired measuring of particle size.

The probe portion 62, which is depicted in FIG. 1 of the drawing, as noted previously herein, comprises one of the principal components of the In Situ Particle Size Measuring Device that forms the subject matter of U.S. patent application Ser. No. 828,840. More specifically, for purposes of obtaining an understanding of the nature of the construction and the mode of operation of the mounting and traversing assembly 10 of the present invention, reference is had to the fact that the probe portion 62 is designed, in a manner yet to be described, to be moved into and out of a flow stream (not shown) in which the particles that are to be measured are to be found. Moreover, in accord with the nature of the construction of the probe portion 62 of the particle size measuring device that forms the subject matter of U.S. patent application Ser. No. 828,840 the probe portion 62 has an opening (not shown) formed therein intermediate the length thereof. This opening (not shown) in turn is designed to be positioned within the flow stream in which the particles to be measured are present such that a portion of the flow stream (not shown) is made to pass through the aforereferenced opening (not shown). Concurrently with the passage of the aforementioned portion of the flow stream (not shown) through the aforereferenced opening (not shown) a light beam is being beamed across the opening (not shown) such that the presence of particles within the opening (not shown) is operative to effect a scattering of any light rays of the light beam that strike particles in the course of crossing the opening (not shown). The extent to which the light rays are scattered as a consequence of having struck particles is a function of the size of the particles that by virtue of having been struck by the particles occasioned the scattering of the light rays. Further, in a manner which is to be found described in detail in U.S. patent application Ser. No. 828,480 it is possible to make measurements of particle size based on the extent to which the light rays are scattered by the particles. It is, therefore, important that the aforereferenced opening (not shown) formed in the probe portion 62 be properly positioned within the flow stream (not shown) which contains the particles in order to ensure that proper measurements are being obtained through the use of the probe portion 62. To this end, one end, i.e., the right end, of the probe portion 62 as best seen with reference to FIG. 1 of the drawing is supported by the flange 56. As such, by varying the positioning of the flange 56 relative to the drive arm 42 it is possible to also adjust the relationship that the probe portion 62 and thereby additionally the relationship that the aforereferenced opening (not shown) bears to the flow stream (not shown) containing the particles that are to be measured.

With further regard to the probe portion 62, the other end, i.e., the left end, thereof as viewed with reference to FIG. 1 of the drawing in a manner well-known to those skilled in the art is suitably received in a packing gland, the latter being denoted in FIG. 1 by the reference numeral 64. More specifically, the probe portion 62 is suitably received in the packing gland 64 so that in a manner yet to be described the probe portion 62 is capable of being made to slide to and fro within the packing gland 64. The packing gland 64 in turn is suitably aligned with an opening (not shown) which is formed in the end plate 32 so as to enable the probe portion 62 to pass therethrough in the course of being made to slide to and fro within the packing gland 64. In addition, the packing gland 64 is suitably secured to a flange, the latter being denoted by the reference numeral 66 in FIG. 1 that is suitably affixed to the inner surface of the end plate 32 by means of any suitable conventional form of fastening means such as the threaded fasteners seen at 68 in FIG. 1 of the drawing.

Turning attention next to the guide means 16, the latter as best seen with reference to FIG. 1 of the drawing includes a shaft denoted in FIG. 1 by the reference numeral 70 which in a manner now to be described is suitably supported within the enclosure 12. More specifically, the shaft 70 is supported within the enclosure 12 so as to extend in substantially parallel but spaced relation to the side plate 28. To this end, the shaft 70 at each end thereof is suitably received in a shaft support, each of the latter being denoted by the reference numeral 72 in FIG. 1. Each of the shaft supports 72 in turn is suitably affixed to the inner surface of the side plate 28 through the use of any conventional form of fastening means such as the threaded fasteners seen at 74 in FIGS. 1 and 3 of the drawing. In accord with the illustrated embodiment of the invention, the shaft 70 is designed to pass through the ball bushing 54 to which reference has previously been had hereinbefore such that the ball bushing 54 in a manner yet to be described can be made to slide to and fro along the shaft 70. As such, the shaft 70 functions as should be readily apparent in the manner of a guide as well as in the manner of a support as the ball bushing 54 slides to and fro therealong. Since as described previously herein the ball bushing 54 is cooperatively associated with the drive arm 42, the shaft 70 can likewise be said to function as a guide and a support for the drive arm 42 as the probe portion 62 is made to undergo movement to and fro relative to the flow stream (not which) that has previously been referred to herein in the course of being inserted therewithin for purposes of making measurements therewith and as the probe portion 62 is thereafter being retracted from the flow stream (not shown) upon completion of the measurement process.

Continuing with a description of the mounting and traversing assembly 10 of the present invention, a description will next be set forth of the movement inparting means 18. As depicted in the drawing, the movement inparting means 18 preferably includes a ball screw, the latter being denoted by the reference numeral 76 in FIG. 1. The ball screw 76, at the left end thereof as viewed with reference to FIG. 1, is designed to be suitably received in a bearing which can be found depicted in FIG. 3 of the drawing wherein the subject bearing is identified by the reference manual numeral 80. The bearing 80 in conventional fashion is supported in a bearing mount, the latter being seen at 82 in FIGS. 1 and 3. As shown in FIG. 1, in accord with the illustrated embodiment of the invention the bearing mount 82 is supported in spaced relation to the inner surface of the end plate 32. In this regard, a single slotted spacer, denoted by the reference numeral 84 in FIG. 1, is preferably interposed between the bearing mount 82 and the inner surface of the end plate 32. Any suitable conventional form of fastening means such as the threaded fasteners seen at 86 in FIG. 1 of the drawing may be employed for purposes of securing the bearing mount 82 as well as the spacer 84 to the end plate 32 such that the bearing mount 82 and the spacer 84 are located within the interior of the enclosure.

Figure 5:
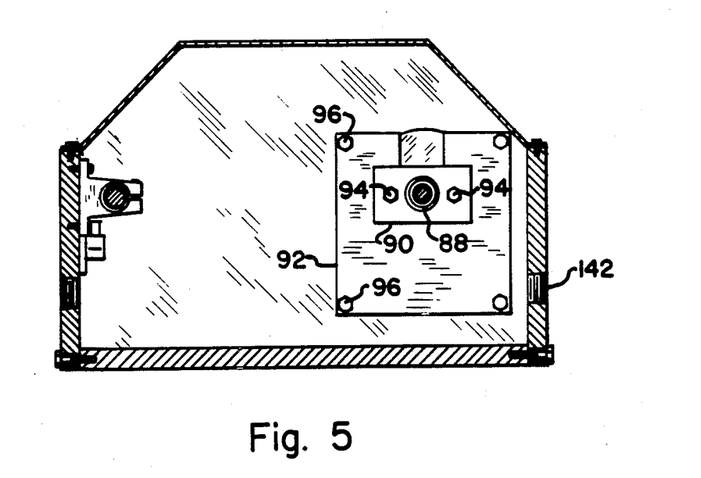
FIG. 5 is a cross-sectional view of the mounting and traversing assembly of FIG. 1 constructed in accordance with the present invention taken substantially along the line 5—5 in FIG. 1.

The other end of the ball screw 76, i.e., the right end thereof as viewed with reference to FIG. 1, is likewise designed to be suitably received in a bearing, the latter being depicted in FIG. 5 wherein the subject bearing is identified by the reference numeral 88. The bearing 88 in turn in known fashion is suitably supported in a bearing mount, the latter being identified by the reference numeral 90 in FIGS. 1 and 5 of the drawing. Continuing, the bearing mount 90 as best understood with reference to FIG. 1 of the drawing is suitably secured to a mounting bracket, denoted by the reference numeral 92 in FIGS. 1 and 5, through the use of any conventional form of fastening means suitable for use for such a purpose. One such form of conventional fastening means which can be employed for this purpose is a plurality of threaded fasteners, the latter being seen at 94 in FIG. 5. Finally, the mounting bracket 92 is itself secured to the inner surface of the end plate 34 by means of conventional threaded fasteners which are identified by the reference numeral 96 in FIGS. 1 and 5.

With reference to FIGS. 4 and 1 of the drawing, it can be seen therefrom that the ball screw 76 intermediate the ends thereof is made to pass through the slot 44 with which as previously described herein the drive arm 42 is suitably provided. Moreover, secured to the drive arm 42 in juxtaposed relation to the slot 44 that is formed therein is a ball nut support, the latter being identified in FIG. 1 by the reference numeral 98. In accord with the illustrated embodiment of the subject matter of the present invention, the ball nut support 98 is secured to the drive arm 42 through the use of conventional threaded fasteners denoted by the reference numeral 102 in FIG. 1. The ball nut support 98 as indicated by its nomenclature is operative as a support for the ball nut, the latter being denoted by the reference numeral 100. As best understood with reference to FIG. 1 of the drawing, the ball nut 100 is designed to be threadedly engaged on the ball screw 76. Further, it can be seen that the ball nut 100 through the ball nut support 98 is operatively connected to the drive arm 42. Thus, by virtue of the relationship that exists between the ball nut 100 and the drive arm 42, in a manner well-known to those skilled in the art the rotation which is imparted to the ball screw 76 in a fashion yet to be described becomes transformed through the action of the ball nut 100 into linear motion which in turn is imparted through the ball nut support 98 to the drive arm 42 and therethrough to the probe portion 62 whereby there is accomplished the insertion and the retraction, to which further reference will be had hereinafter, of the probe portion 62 into the flow stream (not shown) which has been referred to previously herein.

Figure 6:
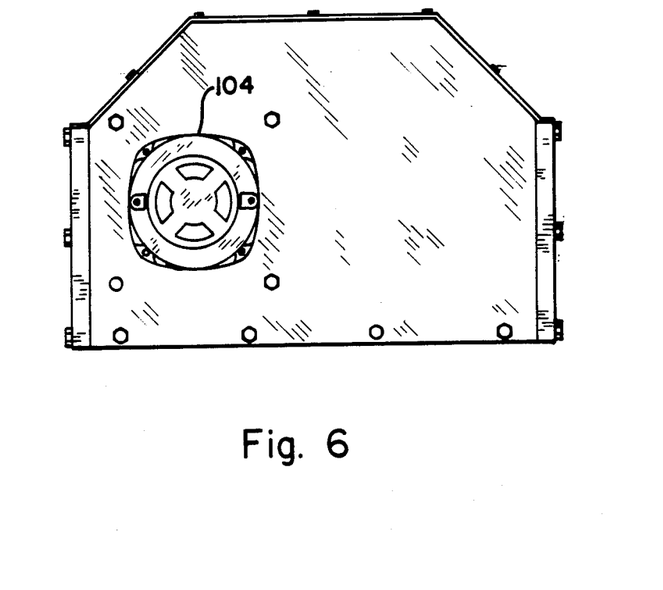
FIG. 6 is a cross-sectional view of the mounting and traversing assembly of FIG. 1 constructed in accordance with the present invention taken substantially along the line 6—6 in FIG. 1.

Rotation of the ball screw 76 is through the operation of the motor means 20. To this end, the motor means 20 includes a gear motor, designated in FIGS. 1 and 6 of the drawing by the reference numeral 104. As depicted in FIG. 1, the gear motor 104 preferably is positioned externally of the enclosure 12. More specifically, as shown in FIG. 1, the gear motor 104 preferably is secured to the outer surface of the end plate 34 through the use of conventional threaded fasteners, the latter being seen at 106 in FIG. 1. The gear motor 104 is operatively interconnected with the right end, as viewed with reference to FIG. 1, of the ball screw 76 through a coupling means, the latter being identified in FIG. 1 by the reference numeral 108, of conventional construction. The coupling means 108 includes a first portion denoted by the reference numeral 110 that is cooperatively associated with the gear motor 104 and a second portion denoted by the reference numeral 112 that is cooperatively associated with the ball screw 76, and in a manner well-known to those skilled in the art is operative to impart rotation from the gear motor 104 to the ball screw 76 both in a first direction whereby the probe portion 62 is caused to be inserted into the flow stream (not shown) and in a second direction whereby the probe portion 62 is caused to be retracted from the flow stream (not shown). Any well-known conventional form of coupling means suitable for use in the aforedescribed manner may be employed as the coupling means 108 in the mounting and traversing assembly 10 which forms the subject matter of the present invention.

In addition to those components which are embodied by the mounting and traversing assembly 10 and that have been described herein thus far, the mounting and traversing assembly 10 in accord with the best mode embodiment of the invention preferably further embodies a first position indicating means 22 and a second position indicating means 24, each of which will now in turn be described. Commencing with a description of the first position indicating means 22, the latter is designed to be operative to provide an indication of the position that the probe portion 62 occupies at any given point in time. To this end, the first position indicating means 22 includes a disk-like member, identified by the reference numeral 114 in FIG. 1, that is suitably mounted relative to the coupling means 108 so as to rotate in sequence with the ball screw 76. The disk-like member 114 in a manner that is well-known to those skilled in the art is suitably provided around the periphery thereof with a plurality of apertures (not shown). Further, the disk-like member 114 is designed to rotate through an opening with which an aperture module, the latter being denoted in FIG. 1 by the reference numeral 116, is suitably provided. The aperture module 116 in turn is suitably secured to the mounting bracket 92 such as by conventional threaded fasteners seen at 118 in FIG. 1. The aperture module 116 which may take the form of any number of devices that are commercially readily available functions in a manner well-known to those skilled in the art to cause a signal beam, which may be in the nature of a beam of light, to be directed across the opening that is formed in the aperture module 116 and through which the disk-like member 114 rotates such that each time an interruption is had of the aforedescribed signal beam of the passage of the solid portion of the disk-like member 114 through the opening with which the aperture module 116 is provided note is made of this fact. Moreover, by noting the number of times that the aforedescribed signal beam has been interrupted and by knowing what the correlation is between each rotation of the ball screw 76 and the amount of linear movement to which the probe portion 62 is subjected per rotation of the ball screw 76, it can then be determined based on the number of interruptions of the signal beam that have been noted and the aforereferenced correlation that exists between the rotational movement of the ball screw 76 and the linear motion imparted thereby to the probe portion 62 what the location of the probe portion 62 is.

Turning next to a discussion of the second position indicating means 24, the latter includes a pair of limit switches identified by the reference numerals 120 and 122, respectively, which are of conventional construction. In addition, the second position indicating means 24 encompasses a pair of switch brackets that are identified by the reference numerals 124 and 126, respectively, in FIG. 1. More specifically, the switch bracket 124 is suitably secured by means of conventional threaded fasteners 128 to the inner surface of the side plate 28 adjacent to the left end of the shaft 70. Further, the limit switch 120 is suitably mounted on the switch bracket 124 so as to be in the path of travel of the ball bushing 54 such that as the ball bushing 54 approaches the limit of its travel relative to the left end, as viewed with reference to FIG. 1, of the shaft 70 contact is made between the ball bushing 54 and the limit switch 120 which has the effect of actuating the limit switch 120. As is well-known to those skilled in the art, this actuation of the limit switch 120 produces an output signal which may be put to a variety of uses such as, for example, causing a stoppage of the gear motor 104 and/or effecting a reversal of the direction of travel of the ball screw 76, etc.

In a similar fashion to that described hereinabove in connection with the discussion pertaining to the switch bracket 124 and the limit switch 120, the switch bracket 126 and the limit switch 122 are suitably mounted adjacent to the right end, as viewed with reference to FIG. 1, of the shaft 70. Namely, the switch bracket 126 is suitably secured by means of conventional threaded fasteners 130 to the inner surface of the side plate 28 adjacent to the right end of the shaft 70. Furthermore, the limit switch 122 is suitably mounted on the switch bracket 126 so as to be in the path of travel of the ball bushing 54 such that as the ball bushing 54 approaches the limit of its travel relative to the right end, as viewed with reference to FIG. 1, of the shaft 70 contact is made between the ball bushing 54 and the limit switch 122 which has the effect of actuating the limit switch 122. As is well-known to those skilled in the art, this actuation of the limit switch 122 produces an output signal which may be put to a variety of uses such as, for example, causing a stoppage of the gear motor 104 and/or effecting a reversal of the direction of travel of the ball screw 76, etc.

The final one of the major components, as enumerated hereinbefore, of the mounting and traversing assembly 10 constructed in accordance with the present invention that remains to be described herein is the mounting means 26. The mounting means 26 is designed to be operative to enable the mounting and traversing assembly 10 to be detachably installed whereby the probe portion 62 of the particle size measuring device with which the mounting and traversing assembly 10 is being utilized is capable of being positioned in the proper location in order that the desired measurements of particle size may be made therewith. One such application for which there exists a need to detachably install the mounting and traversing assembly 10 through the use of the yet to be described mounting means 26 is when the particle size measuring device of which the probe portion 62 forms a part is being utilized in a Pulverized Solid Control System such as that which comprises the subject matter of copending U.S. patent application Ser. No. 828,490, which is assigned to the same assignee as the present invention and which was filed concurrently with the filing of the instant application. To this end, for purposes of obtaining the measurements of particle size required for the operation of the Pulverized Solid Control System which comprises the subject matter of U.S. patent application Ser. No. 828,490, the probe portion 62 of the particle size measuring device is designed to be supported in such a manner as to be insertable and retractable from preferably the coal pipe through which the coal particles after having been subjected to pulverization in a bowl mill are conveyed to the steam generator wherein the coal particles are employed to fire the steam generator. Reference may be had to U.S. patent application Ser. No. 828,490 for a more detailed description of the nature of the construction and the mode of operation of the Pulverized Solid Control System in which the mounting and traversing assembly 10 of the present invention is suited for employment for purposes of accomplishing the mounting and traversing of the probe portion 62 of the particle size measuring device by means of which the measurements of particle size are obtained that are utilized in the Pulverized Solid Control System to which U.S. patent application Ser. No. 828,490 is directed.

Figure 2:
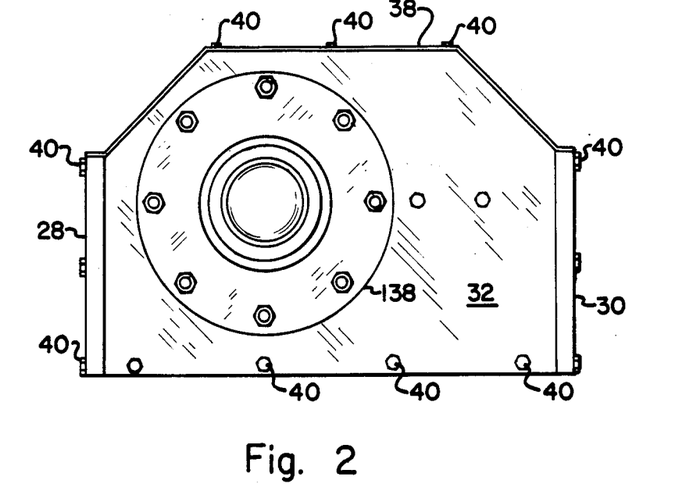
FIG. 2 is a cross-sectional view of the mounting and traversing assembly of FIG. 1 constructed in accordance with the present invention taken substantially along the line 2—2 in FIG. 1.
Figure 3:
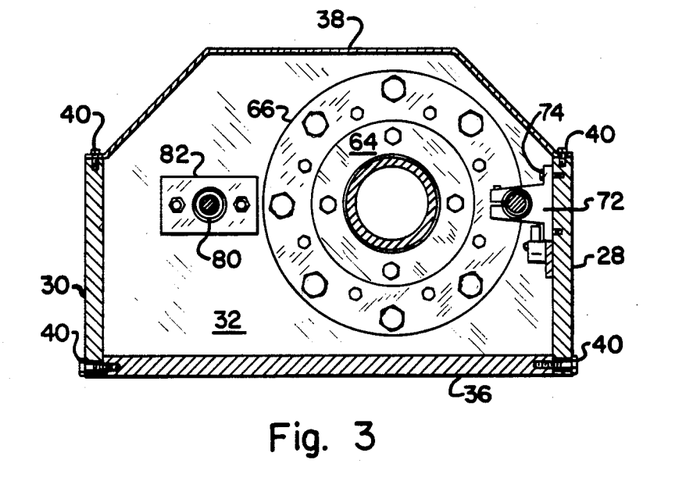
FIG. 3 is a cross-sectional view of the mounting and traversing assembly of FIG. 1 constructed in accordance with the present invention taken substantially along the line 3—3 in FIG. 1.

Proceeding now with a description of the mounting means 26 of the mounting and traversing assembly 10 of the present invention, reference will be had in particular to FIGS. 1 and 2 of the drawing for purposes of the description of the mounting means 26 that follows. Thus, as best understood with reference to FIG. 1 of the drawing, the mounting means 26 includes a lap joint stub end, denoted by the reference numeral 132 in FIG. 1, that terminates in a short nipple, which can be found identified by the reference numeral 134 in FIG. 1. The short nipple 134 is joined to the lap joint stub end 132 in any suitable manner such as, for example, by means of a threaded connection therebetween. Preferably, the short nipple 134 is threaded for at least a portion of the length thereof whereby through the use thereof a threaded connection can be established between the mounting means 26 of the mounting and traversing assembly 10 and whatever other device, such as the coal pipe to which reference has been had hereinbefore, that it is desired to effect the mounting of the mounting and traversing assembly 10 to. The lap joint stub end 132 and thereby also the short nipple 134 that is joined thereto is designed to be supported externally of the enclosure 12. To this end, the lap joint stub end 132 and the short nipple 134 are designed to be positioned in aligned relation to the opening (not shown) with which as previously described herein the end plate 32 is suitably provided in order to accommodate the movement to and fro of the probe portion 62. That is, the probe portion 62 in the course of being inserted into and retracted from the flow stream (not shown) for purposes of making measurements of particle size is designed to slide within the lap joint stub end 132 and the short nipple 134. More specifically, in accord with the illustrated embodiment of the mounting and traversing assembly 10 of the present invention, the lap joint stub end 132 and thereby also the short nipple 134 are preferably secured to the outer surface of the end plate 32 through the use of a flange adaptor seen at 136 in FIG. 1 and a flange denoted by the reference numeral 138 in FIG. 1. As best understood with reference to FIG. 1, the flange adaptor 136 is positioned in abutting engagement with the outer surface of the end plate 32 and the flange 138 is secured in spaced relation to the flange adaptor 136 whereby the lap joint stub end 132 and thereby also the short nipple 134 are supported from the end plate 32 by virtue of the lap joint stub end 132 being held captured between the flange adaptor 136 and the flange 138. Finally, the entire assembly consisting of the flange adaptor 136, the flange 138, the lap joint stub end 132 and the short nipple 134 is in turn secured to the end plate 32 through the use of any conventional form of fastening means such as through the use of conventional threaded fasteners as shown at 140 in FIGS. 1 and 2 of the drawing.

A description will now be had of the mode of operation of the mounting and traversing assembly 10 constructed in accordance with the illustration thereof in FIGS. 1-6 of the drawing. In this connection, it will be assumed for purposes of the following description that the mounting and traversing assembly 10 is being utilized to accomplish the mounting of the probe portion of the In Situ Particle Size Measuring Device, which comprises the subject matter of U.S. patent application Ser. No. 828,480, in order that measurements may be made therewith of the size of coal particles which are needed for purposes of the operation of the Pulverized Solid Control System, which forms the subject matter of U.S. patent application Ser. No. 828,490. To this end, regardless of whether the use of the mounting and traversing assembly 10 is derived from a concern over the wear to which the particle size measuring device might be subjected if the particle size measuring device were to be permanently positioned in the flow stream of the fluid medium containing the particles to be measured, or is derived from the fact that the width of the flow stream of the fluid medium in which the particles to be measured are entrained is sufficiently large as to render it desirable to make measurements with the particle size measuring device of particles at various locations within the aforereferenced flow stream, the mounting and traversing assembly 10 in accord with the present invention is designed to be operative for purposes of effectuating the mounting relative to the flow stream of the probe portion of the particle size measuring device such that the probe portion is capable of being inserted into and retracted from the flow stream. As such, the mounting and traversing assembly 10 must be capable of being detachably installed relative to another device, such as a coal pipe in the case of the application in which for purposes of this description it has been assumed that the mounting and traversing assembly 10 is being employed, with a sufficient degree of rigidity to enable accurate measurements of particle size to be made with the particle size measuring device. Namely, the mounting and traversing assembly 10 must be characterized by its ruggedness whereby the mounting and traversing assembly 10 is capable of being subjected to rugged handling without being adversely affected thereby. In addition, the mounting and traversing assembly 10 must further be characterized by the fact that the mounting and traversing assembly 10 is operative to maintain the proper alignment of the particle size measuring device while measurements are being made therewith of particle size. At the same time, however, the mounting and traversing assembly 10 must be capable of being installed easily and rapidly.

Each of the requirements that are set forth above are satisfied by the mounting and traversing assembly 10 which comprises the subject matter of the present invention. To this end, through the use of the mounting means 26 it is possible to effect a threaded connection between the mounting and traversing assembly 10 and another device such as a coal pipe whereby the mounting and traversing assembly 10 is securely fastened to the aforesaid another device. Moreover, once the mounting and traversing device 10 is securely fastened in the aforedescribed manner to another device such as a coal pipe, the probe portion 62 is capable of being properly oriented relative to the flow stream that contains the particles which it is desired to measure. Such orientation is made possible by virtue of the manner in which the probe portion 62 is supported relative to the drive arm 42; namely, because of the utilization of the arcuate slots 58 and the threaded fasteners 60. Once the probe portion 62 has been deemed to be properly oriented relative to the aforementioned flow stream, the insertion into and retraction from the flow stream is accomplished as a result of the rotation of the ball screw 76, which in turn is driven by the gear motor 104. The rotation of the ball screw 76, as has been described herein previously is transformed, in a manner that is well-known, into linear motion of the drive arm 42 and concomitantly linear movement of the probe portion 62. Further, the mounting and traversing assembly 10 in accord with the best mode embodiment of the invention encompasses a first position indicating means 22 which is operative through the use of a disk-like member 114 to provide an indication of the position occupied by the probe portion 62 at any particular instant in time, and a second position indicating means 24 which is operative through the use of a pair of limit switches 120, 122 to provide an indication of when the drive arm 42, and thus also the probe portion 62, is approaching the limit of its travel in both a first direction and a second direction. Finally, note is made here of the fact that because of the manner in which the mounting and traversing assembly 10 is designed through the use of the mounting means 26 to be detachably installed relative to another device such as a coal pipe, the mounting and traversing assembly 10 is capable of being readily and easily disengaged from the other device when the measurements desired to be made with the particle size measuring device have been obtained whereupon the mounting and traversing assembly 10 can be installed at another location whereat there exists a need to make measurements of particle-size with the particle size measuring device.

Completing the description of the mounting and traversing assembly 10 as illustrated in FIG. 1 of the drawing, it has been found desirable to employ therein a packing gland denoted by the reference numeral 64 in FIG. 1 to which reference has been had hereinbefore; As employed in is designed to serve two functions. First of all, the packing gland 64 is designed to coact with the external surface of the probe portion 62 such as to effectuate a seal therewith whereby to prevent leakage into the interior of the enclosure 12 of the fluid medium in which the particles to be measured are present as the probe portion 62 is being inserted into and retracted from the flow stream. Secondly, the packing gland 64 is designed to be operative to perform a wiping action relative to the external surface of the probe portion 62 for purposes of dislodging therefrom any material which may have been deposited thereon as a result of the probe portion 62 being positioned within the flow stream. With further regard to the matter of leakage of the fluid medium from the flow stream into the interior of the enclosure 12, the enclosure 12 and more specifically the side plate 30 thereof may be suitably provided with a seal air port, the latter being denoted in FIG. 5 of the drawing by the reference numeral 142. The function of the seal air port 142 is to enable control to be exercised over the pressure within the interior of the enclosure 12. To this end, depending upon the nature of the application in which the mounting and traversing assembly 10 is being employed, it may be desirable to pressurize the interior of the enclosure 12 relative to the pressure of the fluid medium in the flow stream whereby any leakage will be from the interior of the enclosure 12 to the flow stream. Such a pressurization of the interior of the enclosure 12 may be effected by supplying a fluid substance such as air to the interior of the enclosure 12 through the seal air port 142. Conversely, if it is desired to have the interior of the enclosure 12 at a lower pressure than that of the fluid medium of the flow stream this may be done simply by lowering the pressure within the interior of the enclosure 12 by withdrawing therefrom through the seal air port 142 a portion of the fluid atmosphere, be it air or some other substance, which exists within the enclosure 12.

Thus, in accordance with the present invention there has been provided a new and improved mounting and traversing assembly suitable for use with devices wherein in connection with the operation thereof the devices are required to be mounted and traversed. Moreover, the mounting and traversing assembly of the present invention is particularly suited for employment with particle size measuring devices wherein it is desired through the use of the particle size measuring devices to obtain therewith measurements in situ of particle size. In addition, in accord with the present invention a mounting and traversing assembly is provided which is suited for employment for purposes of effecting the mounting and traversing of a particle size measuring device particularly in applications in which concern over the wear occasioned by the positioning of the particle size measuring device in the flow stream of the fluid medium containing the particles to be measured, if the particle size measuring device were to be permanently positioned therein, is a consideration. Further, the mounting and traversing assembly of the present invention is suited for employment for purposes of effecting the mounting and traversing of a particle size measuring device particularly in applications in which because the width of the flow stream of the fluid medium in which the particles are entrained is sufficiently large as to render it desirable to make measurements with the particle size measuring device of particles at various locations within the aforereferenced flow stream. Additionally, in accordance with the present invention a mounting and traversing assembly is provided which is particularly suited for employment with a particle size measuring device and which is characterized by the fact that the mounting and traversing assembly is capable of being subjected to rugged handling without being adversely affected thereby. Also, the mounting and traversing assembly of the present invention is particularly suited to be employed with a particle size measuring device and is characterized by the fact that when employed with a particle size measuring device such a mounting and traversing assembly is operative to maintain the proper alignment of the particle size measuring device while the latter is being employed for purposes of making particle size measurements. Furthermore, in accordance with the present invention a mounting and traversing assembly is provided which is particularly suited to be employed with a particle size measuring device, and when being so employed is characterized by the fact that the mounting and traversing assembly is capable of being installed easily and rapidly, while yet being relatively inexpensive to provide.

While only one embodiment of our invention has been shown and described herein, it will be appreciated that modifications thereof, some of which have been alluded to hereinabove, may still be readily made thereto by those skilled in the art. We, therefore, intend by the appended claims to cover the modifications alluded to herein as well as all other modifications which fall within the true spirit and scope of our invention.

What is claimed is:

1. A mounting and traversing assembly for accomplishing the mounting thereof on a surface for effecting, when so needed, the traversing of at least a portion of a device comprising:
   (a) an enclosure consisting of a pair of side members, a pair of end members, a bottom member, a cover member, and means connecting each of said pair of side members to each of said pair of end members and to both said bottom member and said cover member;
   (b) mounted means supported on said enclosure, said mounting means being operative to accomplish the mounting of the mounting and traversing assembly on said surface;
   (c) support means including a drive arm mounted within said enclosure so as to extend substantially perpendicular to each of said pair of side members, said drive arm being operative to support at least a portion of the device for movement into and out of said enclosure through one of said pair of end members;
   (d) guide means including a shaft supported within said enclosure in spaced relation to one of said pair of side members and so as to extend in substantially parallel relation thereto, said shaft being operatively connected to said drive arm so as to be operative as a guide for said drive arm when the portion of the device supported by said drive arm is being moved into and out of said enclosure through said one of said pair of end members;
   (e) movement imparting means supported within said enclosure in sapced relation to the other one of said pair of side members and so as to extend in substantially parallel relation thereto, said movement imparting means comprises a ball screw operatively connected to said drive arm so as to be operative to impart motion to said drive arm;
   (f) a power source supported on said enclosure, said power source comprises a gear motor operatively connected to said ball screw so as to be operative to provide power to said ball screw; and
   (g) position indicating means supported within said enclosure, said position indicating means includes a first position indicating means operative to provide an indication of the position occupied at any given point in time by the portion of the device supported by said drive arm, said first position indicating means including a rotatable disk-like member having a plurality of apertures formed around the periphery thereof.

2. The mounting and traversing assembly as set forth in claim 1 wherein said position indicating means further includes a second position indicating means operative to provide an indication of when the portion of the device supported by said drive arm reaches the limit of its travel in either of two directions.

3. The mounting and traversing assembly as set forth in claim 2 wherein said mounting means includes a lap joint stub end having a short nipple threadedly interconnected thereto, said lap joint stub end and said short nipple being mounted on the exterior surface of said one of said pair of end members.

4. A mounting and traversing assembly for accomplishing the mounting thereof on a surface for effecting, when so mounted, the traversing of the probe portion of a particle size measuring device comprising:
   (a) an enclosure consisting of a pair of side members, a pair of end emmbers, a bottom member, a cover member, and means connecting each of said pair of side members to each of said pair of ends members to both said bottom member and said cover member;
   (b) mounting means supported on said enclosure, said mounting means being operative to acommplish the mounting of the mounting and traversing assembly on said surface;
   (c) support means including a drive arm mounted within said enclosure so as to extend substantially perpendicular to each of said pair of side members, said drive arm being operative to establish the orientation of the probe portion of the particle size measuring device for purposes of enabling measurements to be made therewith of particles size;
   (d) guide means including a shaft supported within said enclosure in spaced relation to one of said pair of side members and so as to extend in substantially parallel relation thereto, said shaft being operatively connected to said drive arm so as to be operative as a guide for said drive arm when the probe portion of the particle size measuring device supported by said drive arm is being subject to movement within said enclosure for purposes of enabling measurements to be made therewith of particle size;

(e) movement imparting means supported within said enclosure in spaced relation to the other one of said pair of side members and so as to extend in substantially parallel relation thereto, said movement imparting means comprises a ball screw operatively connected to said drive arm so as to be operative to impart motion to said drive arm;

(f) a power source supported on said enclosure, said power source comprises a gear motor operatively connected to said ball screw so as to be operative to provide power to said ball screw; and (g) position indicating means supported within said enclosure, said position indicating means includes a first position indicating means operative to provide an indication of the position occupied at any given point in time by the probe portion of the particle size measuring device supported by said drive arm, said first position indicating means including a rotatable disk-like member operatively coupled to said ball screw, said rotatable disk-like member having a plurality of apertures formed around the periphery thereof.

5. The mounting and traversing assembly as set forth in claim 4 wherein said position indicating means further includes a second position indicating means operative to provide an indication of when the probe portion of the particle size measuring device supporting by said drive arm reaches the limit of its travel in either of two directions.

6. The mounting and traversing assembly as set forth in claim 5 wherein said mounting means includes a lap joint stub end having a short nipple threadedly interconnected thereto, said lap joint stub end and said short nipple being mounted on the exterior surface of said one of said pair of end members.

* * * * *